United States Patent [19]

Roesler et al.

[11] Patent Number: 5,462,692
[45] Date of Patent: Oct. 31, 1995

[54] STABLE SOLID ACETYLPEROXYBORATE COMPOUNDS

[75] Inventors: Richard Roesler, Rheinbrohl; Siegfried Schelle, Puchheim; Michael Gnann, Pfaffenhofen; Werner Zeiss, Groebenzelli, all of Germany

[73] Assignee: Peroxid-Chemie GmbH, Hoellriegelskreuth, Germany

[21] Appl. No.: 801,001

[22] Filed: Dec. 2, 1991

[30] Foreign Application Priority Data

Nov. 30, 1990 [DE] Germany ............... 40 38 202.8

[51] Int. Cl.$^6$ ............... C01B 15/12; C01B 15/022; C07F 5/02
[52] U.S. Cl. ............... 252/186.26; 252/99; 252/186.23; 252/186.3; 252/186.28; 252/186.29; 423/280; 423/281; 423/282; 568/1; 568/6; 568/566
[58] Field of Search ............... 252/186.3, 186.23, 252/99, 186.26, 186.28, 186.29; 568/1, 6, 566; 423/281, 280, 282

[56] References Cited

U.S. PATENT DOCUMENTS

| | | | |
|---|---|---|---|
| 4,126,717 | 11/1978 | Mazzola | 427/220 |
| 4,133,637 | 1/1979 | Blumbergs et al. | 8/104 |
| 4,338,260 | 7/1982 | Schirmann | 252/90 |
| 4,391,723 | 7/1983 | Bacon et al. | 252/90 |
| 5,049,298 | 9/1991 | Ploumen et al. | 423/584 |
| 5,154,912 | 10/1992 | Shirmann et al. | 423/584 |

FOREIGN PATENT DOCUMENTS

| | | |
|---|---|---|
| 549015 | 11/1942 | United Kingdom . |
| 550490 | 11/1943 | United Kingdom . |
| 561180 | 5/1944 | United Kingdom . |

OTHER PUBLICATIONS

*Advanced Organic Chemistry: Reactions, Mechanisms, and Structure* 3rd edition, Jerry March, John Wiley and Sons Inc. 1985.

Primary Examiner—Philip Tucker
Assistant Examiner—Valerie Fee
Attorney, Agent, or Firm—Evenson, McKeown, Edwards & Lenahan

[57] ABSTRACT

Stable, solid acetyl peroxyborate compounds which are active oxygen-containing compounds derived from acetic acid and boron-oxygen compounds. The compounds of the invention have a peracetic acid content which can be liberated instantly and directly in water with only minor formation of hydrogen peroxide The acetyl peroxyborates of the invention are useful in washing, bleaching and cleaning agent and disinfectant applications and as oxidizing agents in organic synthesis.

41 Claims, No Drawings

STABLE SOLID ACETYLPEROXYBORATE COMPOUNDS

BACKGROUND OF THE INVENTION

The present invention relates to new, stable, solid acetyl peroxyborate compounds (compounds containing active oxygen and derived from acetic acid and boron-oxygen compounds), a process for producing such acetyl peroxyborate compounds, and to detergent, bleaching agent, cleaning agent and disinfectant compositions as well as oxidizing agents for use in organic synthesis, which compositions contain such acetyl peroxyborate compounds.

Both inorganic and organic active oxygen compounds are used in detergents, bleaching agents and cleaning agents, particularly those used for textiles, in disinfectants and as oxidizing agents. Examples of such active oxygen compounds include perborates, persulfates, mono and diperoxycarboxylic acids and, in particular, perborate/activator combinations which form peracetic acid in situ.

In comparison with pure inorganic percompounds, such as perborate, the peroxycarboxylic acids, such as e.g. diperoxydodecanedioic acid (DPDDA) or peracetic acid, and perborate/activator combinations, such as perborate/TAED systems, are characterized by a low effective temperature and a high bleaching and disinfectant power. Also, it is well known in the art that perborates and peroxycarboxylic acids can be used in chemical synthesis as oxidizing agents for oxidizing organic compounds.

The use of suitable peroxycarboxylic acids for the aforementioned applications is therefore increasingly desirable. Although progress in the use of peroxycarboxylic acids has been made by the development and marketing of peroxycarboxylic acids and/or combinations of perborates and activators which form peroxycarboxylic acids, there remain disadvantages to be overcome with respect to the utilization of peroxycarboxylic acids and/or activators which form peroxycarboxylic acids.

For many applications, the only peroxycarboxylic acids that are generally suitable are those which are solid at room temperature, i.e. fairly long-chain aliphatic peroxycarboxylic acids such as DPDDA which, however, has a poor solubility in water. In addition, peroxycarboxylic acids are thermally and mechanically sensitive in the pure or highly concentrated states, and solid peroxycarboxylic acids must therefore be stabilized by suitable desensitizing agents, e.g. hydrate-forming inorganic salts such as sodium sulfate. A disadvantage in this regard is that the stability of the desensitized solid peroxycarboxylic acids is influenced considerably by the type and method of peroxycarboxylic acid production and by the desensitization. In addition, long-chain peroxycarboxylic acids may be harmful to the environment because of the long hydrocarbon chain.

In comparison, peracetic acid—being a short-chain peroxycarboxylic acid with only two carbon atoms—is safe for the environment and has good water solubility. However the disadvantage of peracetic acid is that it is liquid at room temperature. In addition, it can only be produced as a solution of peracetic acid in acetic acid, but not in pure form. As a result, the possibilities for using peracetic acid as such are limited. To eliminate this disadvantage, activators such as tetraacetylethylenediamine (TAED) have been developed in the prior art, which are capable of forming peracetic acid in situ in the presence of persalts such as perborate. In this case, however, it is a disadvantage that $H_2O_2$ must initially be formed from the persalt, which produces the peracetic acid only subsequently by reaction with the activator. However, the formation of peracetic acid can be adversely affected by premature decomposition of the hydrogen peroxide formed in situ. In order to be able to better utilize the advantages of peracetic acid there is therefore a need for a simple, stable, non-deliquescent active oxygen compound with an oxidizing and/or bleaching effect, which is based on a short-chain acetic acid.

SUMMARY OF THE INVENTION

It is the object of the invention to provide solid acetylperoxyborate compounds which contain active oxygen and liberate peracetic acid with its high oxidizing, bleaching and disinfecting effect during use.

Another object of the invention is to provide solid acetylperoxyborate compounds which overcome the aforementioned disadvantages of the prior art.

A further object of the invention is to provide solid acetylperoxyborate compounds which are chemically and physically stable and which are safe to handle.

Yet another object of the invention is to provide solid acetylperoxyborate compounds which can be used as effective active oxygen components in detergents, bleaching and cleaning agents and disinfectants and/or as an effective oxidizing agent.

It is also an object of the invention to provide solid acetylperoxyborate compounds which can be produced in a simple manner.

These and other objects of the invention are achieved by providing a solid acetyl peroxyborate compound having an active oxygen content of from 2 to 8% by wt.; a peracetic acid content, which can be liberated upon dissolution of the acetyl peroxyborate compound in water, of at least 10% by wt., and a hydrogen peroxide content of less than 4% by wt.

DETAILED DESCRIPTION OF PREFERRED EMBODIMENTS

The invention provides new solid acetyl peroxyborate compounds, i.e. active oxygen-containing compounds based on acetic acid and boron-oxygen compounds, which are characterized by an active oxygen content of 2 to 8% by weight; by a peracetic acid content, which is liberated when the acetyl peroxyborate compound is dissolved in water, of at least 10%, preferably 10 to 30%, by weight, and by a hydrogen peroxide content of less than 4% by weight.

The acetyl peroxyborate compounds according to the invention are colorless, solid compounds and are characterized by an extraordinarily favorable active oxygen stability. They are chemically and physically stable during storage and handling at normal temperatures. This is a substantial safety advantage with regard to production, processing and use. The compounds of the invention accordingly have high decomposition temperatures and have proved to be mechanically and/or thermally stable both in the drop hammer test (>5 mkg) and in the steel cartridge test (<1 mm/Koenen test). The compounds according to the invention are consequently not impact sensitive and are not explosive. It is thus possible for the first time to bind peracetic acid in a stable solid form from which it can be easily liberated in a simple manner during use in an aqueous medium.

The solid acetyl peroxyborate compounds according to the invention are readily water-soluble and liberate peracetic acid immediately and directly on dissolution in water, but only a little hydrogen peroxide. The hydrogen peroxide content that can be liberated from the acetyl peroxyborate compounds according to the invention is thus less than 4% by weight. Particularly advantageous acetyl peroxyborate compounds according to the invention are characterized in that the hydrogen peroxide content that can be liberated on dissolution of the acetyl peroxy compound in water is less than 3% by weight, preferably less than 1.5% by weight. In contrast, the peracetic acid content that can be liberated from the acetyl peroxyborate compounds according to the invention is at least 10% by weight, in particular 10 to 30% by weight. Preferred acetyl peroxy borate compounds according to the invention are characterized in that the content of peracetic acid that can be liberated on dissolution of the acetyl peroxyborate compound in water is 20 to 30% by weight.

No precise molecular structure can be determined for the acetyl peroxyborates according to the invention. However, based on their chemical origin and/or manufacture and on their properties, the compounds according to the invention can be defined as being active oxygen-containing compounds composed of acetic acid and boron-oxygen compounds. These "acetyl peroxyborates" consequently contain structural elements which are derived from the starting educts used in their manufacture, namely acetyl groups, active oxygen and borate structures:

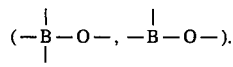

The acetyl groups originate from the underlying acetic acid and/or peracetic acid. The active oxygen originates from the underlying active oxygen carrier, e.g. $H_2O_2$, perborate, or peracetic acid. The borate structures present in the compounds according to the invention arise during the formation of the compounds of the invention from the underlying boron-oxygen compounds, but may be transformed during the formation of the compounds of the invention so that they need not correspond in structure and arrangement to the underlying boron-oxygen compounds. As a result of the peracetic acid content which can be liberated on dissolution of the solid compound in water, which peracetic acid is presumably at least partly structurally pre-formed in the compounds, the compounds of the invention can also be referred to as solid peracetic acid derivatives (compounds which release peracetic acid) and/or as a "solid peracetic acid".

The acetyl peroxyborate compounds according to the invention differ substantially from the starting compounds as regards their macroscopic appearance, their chemical and their physical properties. The physical properties of the acetyl peroxyborate compounds according to the invention include an IR spectrum with characteristic IR bands at approximately 1650 to 1670 cm$^{-1}$ and at approximately 1740 to 1755 cm$^{-1}$ (measured in potassium bromide and/or potassium chloride). In contrast, products free of active oxygen obtained by reacting boron-oxygen compounds free of active oxygen (e.g. borax) with acetic acid, exhibit no IR bands in these regions, but merely at approximately 1580 cm$^{-1}$. In addition, the compounds of the invention exhibit a characteristic $^{13}$C-NMR band in the NMR spectrum ($^{13}$C-CP/MAS-NMR, solid body spectroscopy: CP=cross polarization, MAS=magic angle spinning) at 18 to 19 ppm, i.e. at approximately 18.5 ppm [measured against tetramethylsilane (TMS) as an external standard]. When analyzed by differential scanning calorimetry, the compounds of the invention exhibit a characteristic differential calorimetry diagram which is endothermic at approximately 135° to 140° C. and changes to exothermic with an exothermic peak-maximum at approximately 170° to 185° C. As can be seen from this high decomposition temperature, the compounds of the invention have a low temperature sensitivity and are characterized by high thermal stability. Their thermal stability exceeds the stability of known persalts such as sodium percarbonate, sodium perborate monohydrate or sodium perborate tetrahydrate, which exhibit differential calorimetry diagrams with exothermic decomposition peaks at temperatures of 140° to 160° C. Their thermal stability also exceeds that of known peroxycarboxylic acids such as DPDDA, whose differential calorimetry diagram exhibits an exothermic decomposition peak at temperatures as low as approximately 130° C.

The solid acetyl peroxyborate compounds according to the invention make peracetic acid available for the first time in an application form which is solid at standard ambient conditions, has excellent stability, and is in an advantageous form for application. This solid application form of peracetic acid can be used with advantage in detergent, cleaning agent, bleaching agent and disinfectant compositions and as an oxidizing agent in organic synthesis, Consequently, the invention also relates to detergent, cleaning agent, bleaching agent and disinfectant compositions and oxidizing agents for organic synthesis, which contain an acetyl peroxyborate compound according to the invention. The acetyl peroxyborate compounds according to the invention can be used particularly advantageously in solid bleaching agent and disinfectant compositions as compounds which give off peracetic acid. In a further aspect, the invention consequently includes solid bleaching agent and disinfectant compositions which contain a peroxyborate compound according to the invention. Compositions which contain the acetyl peroxyborate compounds of the invention in the form of powders or granular products in a sachet or in the form of tablets fused into a film are particularly advantageous in this regard. The acetyl peroxyborate compounds according to the invention can, for example, be used advantageously in dry bleach and as a solid disinfectant that is easy to meter and adjust to the desired concentration during use in aqueous solution.

It is particularly advantageous to use the acetyl peroxyborate compounds according to the invention as disinfectants in the form of a powder, granular product, etc., in a sachet, or in the form of a tablet fused into a film, since these forms greatly facilitate use of the peracetic acid as a disinfectant in cases where aqueous solutions containing specific amounts of peracetic acid are to be prepared by the user. Previously, for example, when preparing such aqueous peracetic acid disinfectant solutions it has been necessary during dosage to measure out a concentrated, highly corrosive peracetic acid/acetic acid solution having a pungent odor and to dilute it to the desired concentration with water, a procedure which required special safety measures and specially trained personnel. Compounds according to the invention in the form of a sachet and/or a tablet fused in a film can be used to prepare aqueous disinfectant solutions and/or a desired dosage of a disinfectant in a simple manner in that the content of a sachet or a tablet merely needs to be introduced into a predetermined amount of water. Thus it is simple, convenient and fairly safe for a user to prepare and use such disinfectant solutions.

The invention also relates to a process for producing the acetyl peroxyborate compounds according to the invention, comprising reacting:

a) a solid boron-oxygen compound with acetic acid and hydrogen peroxide, and/or b) a solid boron-oxygen compound with a solution of peracetic acid in acetic acid, and/or c) a solid peroxygen-containing boron-oxygen compound with acetic acid, to produce a viscous solution, suspension or paste, and drying the viscous solution suspension or paste to recover the resulting acetyl peroxyborate compound. Optionally, acetic anhydride may be added to the reacting step. In process variants a) and b), an alkaline sodium salt optionally may be added.

The acetyl peroxyborate compounds according to the invention can be produced very simply according to the above-mentioned three process variants a), b) and c) by mixing and reacting the respective reactants and optional additives using standard equipment (e.g. mixers, dryers etc.). The reactions in these process variants are advantageously carried out at temperatures of up to 60° C., preferably at temperatures of 30° to 45° C.

The quantities of reactants used are advantageously adjusted to each other in such a way that in process variant a) the molar ratio of boron to acetyl groups to heydrogen peroxide is 1:(1 to 5):(0.2 to 2);

in process variant b) the molar ratio of boron to peracetic acid is 1:(0.2 to 2), preferably 1:(0.5 to 1), and in process variant c) the molar ratio of peroxygen-containing boron-oxygen compound to acetyl groups is 1:(1 to 10), preferably 1:(2 to 6).

Known solid boron-oxygen compounds can be used as the starting educts in process variants a) and b). Examples of these include, in particular, boric acid, boron oxide ($B_2O_3$) or polyborates such as e.g. borax ($Na_2B_4O_7$ with up to 10 molecules of water of hydration), sodium metaborate and sodium metaborate hydrate. Boron-oxygen compounds containing little or no water of hydration, such as boron oxide, and polyborates containing little or no water of hydration, such as borax with up to 3 molecules of water of hydration (e.g. borax dihydrate or borax trihydrate) or borax anhydride ($Na_2B_4O_7$) are advantageous. Boron oxide, which reacts outstandingly, (for example, with sodium acetate added as alkaline sodium salt) and, for economic reasons, the so-called borax B ($Na_2B_4O_7$ with approximately 2 to 3 molecules of water of hydration) and/or the so-called borax C ($Na_2B_4O_7$ with approximately 0 to 1 molecule of water of hydration) are especially preferred. Borax types B and C can be prepared from the so-called borax A (borax decahydrate having the formula $Na_2B_4O_7 \cdot 10H_2O$) by known dehydration processes. Borax B, for example, is obtained from borax A by 2 hours drying at 150° C. in a circulating air oven. To obtain borax C, the resulting borax B is additionally dried for 1 hour at 400° C. In process variant a), the acetyl peroxyborate product according to the invention is formed directly from simple starting educts, i.e. from boron-oxygen compound, acetic acid and hydrogen peroxide as well as optional acetic anhydride and optional alkaline sodium salt via peroxygen-containing boron-oxygen compounds (perborates) formed as intermediate products and/or via peracetic acid formed as an intermediate product. To form the acetyl peroxyborate product according to the invention in process variant b), the boron-oxygen compound used is reacted with a pre-formed peracetic acid (as a peracetic acid solution in acetic acid), whereby the crystalline forms of the boron-oxygen compounds are particularly advantageous.

Known solid peroxygen-containing boron-oxygen compounds (e.g. perborates or peroxyborates, superoxidized perborates) can be used as starting educts for process variant c). In particular, perborates which are free from or have a low content of water of hydration and which have a molar ratio of Na:B of 0.3:1 to 1:1 are advantageously used. As used herein, the term "low content of water of hydration" means a water of hydration content of at most 3 water molecules. Sodium perborate monohydrate and sodium perborate with an Na:B molar ratio of 0.4:1 to 0.7:1 are particularly preferred perborates. If perborates with an unconventional Na:B molar ratio of 0.45:1 to 0.65:1 are used, advantageous acetyl peroxyborate products with a high content of liberatable peracetic acid are obtained.

The reaction for producing the acetyl peroxyborate compounds according to the invention takes place in a fairly simple manner by mixing the starting compounds and allowing them to react. If desired, acetic anhydride is added, in particular to take up water; or if desired, an alkaline sodium salt is added in order to obtain a desired Na:B molar ratio. If only boron oxide and/or boric acid is used as the boron-oxygen compound, then in every case an alkaline sodium salt is added to obtain the desired Na:B molar ratio. Suitable alkaline sodium salts include sodium hydroxide, sodium carbonate, sodium acetate, sodium phosphates, or other alkaline sodium salts. Sodium carbonate or sodium acetate is particularly advantageous. During the reaction, a viscous solution, suspension or paste is formed which is agitated or kneaded with heating or, in appropriate cases, with a spontaneous increase in temperature. The time which is appropriate or required for the conversion can vary depending on the process variant. According to process variant c), the conversion time can be as long as 100 hours, preferably 5 to 30 hours. According to process variant a) the conversion time can be 50 hours, preferably 2 to 20 hours. According to process variant b), the conversion time can range from very short periods up to 10 hours, but preferably from very brief reaction times to 5 hours. In the most advantageous case, the reaction mixture can be dried immediately after mixing the reactants to remove excess acetic anhydride and/or glacial acetic acid in order to obtain the acetyl peroxyborate compound.

Moreover, in the reactions of variants a) to c) it has proved advantageous, particularly with regard to obtaining a high content of liberatable peracetic acid and a stable product, to add as little water as possible during the conversion. When selecting the starting materials, care should therefore be taken to ensure that as little water as possible is introduced into the reaction together with the starting materials. Not only are oxygen- or peroxygen-containing boron oxygen compounds which contain little or no water of hydration preferred, as mentioned above, but also the other starting materials such as, in particular, acetic acid, hydrogen peroxide (e.g. with an $H_2O_2$ content of >50% by weight) and the solutions of peracetic acid in acetic acid used are used in their low water content forms. According to particularly preferred embodiments of process variant a), a hydrogen peroxide solution containing at least 70% by weight $H_2O_2$ is used. In process variant b), a solution of peracetic acid in acetic acid, containing as little water as possible, is used. For this reason, peracetic acid solutions are particularly preferred which are prepared from acetic acid and/or acetic anhydride and hydrogen peroxide with an $H_2O_2$ content of at least 50% by weight, preferably at least 70% by weight. According to the highly advantageous process variant b) it is therefore recommended to use, in particular, pre-formed peracetic acid solutions containing approximately 21.5% by weight peracetic acid, 0.5% by weight hydrogen peroxide, 71.5% by weight acetic acid, and at most approximately 6.5% water. The water content can optionally be reduced further by adding acetic anhydride.

In accordance with advantageous embodiments of the invention, conventional stabilizers for percompounds are added during production of the acetyl perborate compounds of the invention, or they may already be present in the starting materials used. The stabilizers can also be added after the conversion is completed and before the drying step. Suitable stabilizers include phosphates such as metaphosphate, organic stabilizers such as quinolinic acid, salicylic acid or dipicolinic acid (DPA), chelating agents such as 8-oxyquinoline or ethylene diamine tetraacetic acid (EDTA), phosphonic acid derivatives such as methylene and/or aminomethylene phosphonic acids or the salts thereof as well as small quantities of the usual wetting agents. Especially suitable stabilizers, particularly with regard to long term stability of the products of the invention, include, for example, 1-hydroxyethane-1,1-diphosphonic acid, ethylenediamine tetramethylene phosphonic acid, dietheylenetriamine pentamethylene phosphonic acid, and the salts thereof. Such stabilizers can be incorporated into the product of the invention in the usual concentrations of 0.1 to 10 g/kg. If the stabilizers are introduced during the preparation of the acetyl peroxyborate compounds of the invention, this can preferably take place via the hydrogen peroxide solution or the peracetic acid solution used. In particular, the stabilizers are used in quantities corresponding to the amounts required to be present for effective subsequent stabilization of the products.

The conversion of the starting materials to the acetyl peroxyborate compounds according to the invention can be carried out in known apparatus. For example, the conversion can take place with stirring in glass, enamel or polyethylene vessels equipped with stirrers. Initially free-flowing solutions or suspensions are obtained which gradually become more viscous or paste-like and which, in this still pumpable state, can be transferred into drying equipment to remove the water and excess acetic acid. The conversion can also advantageously be carried out in high-speed vacuum intensive mixers in which the subsequent drying operation can also take place. In this way, round granular products having a grain size of 1 to 3 mm are obtained. Fines which may be formed can be removed by subsequent sieving and optionally conveyed to further granulation stages. Turbulence mixers (mixing mills with adjustable grain size) which permit better control of the grain size of the product can also advantageously be used.

According to another highly advantageous embodiment of the process for producing the acetyl peroxyborate compounds of the invention, the acetyl peroxyborate compounds obtained in paste from or by intermediate drying are washed with an inert solvent before final drying. Particularly preferred solvents for this include lower alcohols such as C1- to C3-alcohols (methanol, ethanol, propanol, isopropanol) or esters of these alcohols with acetic acid. Among the lower alcohols, ethanol is particularly preferred, and among the acetate esters, ethyl acetate is particularly preferred. Particularly advantageous products can be obtained in this way. Industrial solvents which need not be completely anhydrous can also be used for washing.

Following the conversion or after optional intermediate drying and washing, water, excess acetic acid used, and residues of any inert solvent used for washing are removed in a known manner (e.g. by circulating air drying, vacuum drying, roller drying, spray drying, fluid bed drying, etc.) from the reaction mixture, which generally is obtained in the form of a viscous solution, suspension or paste.

Drying is carried out under known conditions suitable for peroxygen-containing compounds. Appropriate conditions, particularly the drying temperature, depend on the type of drying process used and on the residence time of the respective solid acetyl peroxyborate product in the dryer.

Spray drying processes, for example, provide a gentle and rapid method for preparing the product. Spray drying is also suitable for producing fairly large quantities of product. Viscous solutions or suspensions obtained during the reaction can either be used directly for spray drying, or pastes obtained during the reaction can be spray dried after conversion into a sprayable suspension. Pastes are converted to sprayable suspensions by adding inert solvents such as those used for the wash process described above, for example by adding ethyl acetate. Any spray drying process can be used. For example, standard spray dryers (SD) or special dryers such as spin-flash dryers, which are also suitable for drying pastes without conversion into a suspension, can be used as well as fluid bed spray dryers (FSD) or fluid bed spray granulators (FSG). In addition to drying the product, the latter two also permit the product to be granulated in conjunction with the drying step. The drying temperatures (off-gas temperatures) depend on the residence time of the product in the dryer. For short residence times such as occur in a spray dryer, drying temperatures of approximately 80° to 130° C., preferably 95° to 115° C., are suitable. In the case of longer residence times such as occur in a fluid bed spray granulator (FSG), the drying temperatures may suitably be 50° to 90° C.

The acetyl peroxyborates according to the invention can also be dried in another way in a stream of air, e.g. in fluid bed or circulating air dryers. In such a case, the drying temperatures generally amount to 30° to 80° C., preferably 40° to 60° C. Another possibility is vacuum drying which leads in particular to very high liberatable peracetic acid contents in the product. Suitable drying temperatures during vacuum drying under a water-jet vacuum or at pressures of approximately 15 to 100 mbar are 30° to 80° C., preferably 40° to 60° C.

It is also possible to combine different drying processes. This can be particularly advantageous if the products are to undergo intermediate drying in order to be washed with inert solvents. The products thus can be initially pre-dried to a certain level, e.g. by vacuum drying, and subsequently washed with an inert solvent and finally dried in a stream of air, for example in a fluid bed dryer or a circulating air dryer as described above.

Moreover, with special equipment it is possible to carry out both the reaction of the starting materials, the granulation of the resulting product, and the final and/or intermediate drying as a "one pot process" in a vacuum mixer suitable for granulation, e.g. in a vacuum intensive mixer.

In a particularly preferred embodiment of the above-described process variant b) for producing the acetylperoxyborates according to the invention, the reaction of the boron-oxygen compound with a pre-formed peracetic acid solution is carried out in specially equipped mixers in such a way that particulate acetylperoxyborate is already obtained within short reaction and crystallization times. This process for producing solid acetylperoxyborate compounds is characterized in that in a mixer which is equipped with a rotating mixing tool, a size-reducing auxiliary mixing tool, a heat exchanger for cooling and heating, and a vacuum device, whereby at least the size-reducing auxiliary mixing tool is characterized by a Froude number $Fr>1$, preferably $Fr>>1$, b1) a pre-formed solution of peracetic acid in acetic acid and a boron-oxygen compound with a low water content are reacted with each other in such a way that the temperature does not exceed about 40° C., b2) seed crystals of acetylperoxyborate are added, b3) while mixing at temperatures of up to about 45° C., a paste of the acetylperoxyborate is formed, b4) a lubricant is optionally added to the paste, and the paste is pre-dried under vacuum at a product temperature of up to about 60° C., preferably from 35° to 55° C., until a granular acetylperoxyborate forms, whereby in the course of this pre-drying, after exceeding a break down or changeover phase at the onset of disintegration of the substantially pre-dried paste of acetyl peroxyborate, the size-reducing auxiliary mixing tool is turned on for a brief period of time, and b5) subsequently either b5.1) the pre-dried acetylperoxyborate is completely dried at standard pressure and at a product temperature of up to about 80° C., preferably up to about 60° C., and thereafter the desired particle size fraction of the acetylperoxyborate is separated by sieving, or b5.2) initially separating the desired particle size fraction of the acetylperoxyborate from the coarse and/or fine portions by sieving the pre-dried acetylperoxyborate, and subsequently completely drying only the fraction having the desired particle size at normal pressure and at a product temperature of up to about 80° C., preferably up to about 60° C., whereby the acetylperoxyborate is obtained in the form of a solid, granular and free-flowing particulate material.

In the foregoing embodiment of process variant b), the reaction of boron-oxygen compound with peracetic acid is carried out in specially equipped vacuum mixers, e.g. vacuum turbulence mixers or vacuum intensive mixers, which are provided with at least one high-speed rotating mixing or size-reducing tool which rotates at high speed, characterized by a Froude number of greater than one (>1), preferably by a Froude number much greater than 1 (>>1), whereby a large Froude number is particularly important for forming a particulate material after the break down or changeover phase described below. The Froude number is thus an index of the movement of material in a ribbon blender (forced mixer) and describes as an order of magnitude the interplay between inertial forces and gravity forces. The Froude number Fr is therefore utilized to characterize mixing processes or to classify mixers into various types. It is defined as $Fr=Rw^2/g$, wherein R represents the outer radius of the mixing element, W represents the angular speed, and g equals the acceleration of gravity.

The types of mixers which are used must have a heat exchanger device which permits both cooling and also heating for controlling the temperature during the reaction and drying. For example the mixer may be equipped with a double jacket suitable for both cooling and heating.

In addition to the rotating tool which is constructed as a plowshare mixer or wing mixer, the mixers which are used additionally have high-speed rotating auxiliary mixers for size reduction, which are constructed, for example, as studded disc mills. The types of mixers which are used are thus equally suited for mixing, size reduction and for rounding as well as for vacuum drying the product. Therefore, reaction, crystallization, drying and granulation can be carried out in a single apparatus (one pot process).

In the reaction in accordance with the foregoing embodiment of process variant b), the peracetic acid solution is reacted in the mixer with a solid boron-oxygen compound in the form of a powder or granules. Both the peracetic acid and also the boron-oxygen compound are thereby utilized in forms with low water contents. The water content introduced with the reactants into the pre-formed peracetic acid solution can easily be decreased by addition of acetanhydride during the formation of peracetic acid. For this purpose, acetanhydride is added in up to an approximately equimolar amount to the water content of the reactants which serve for the production of the peracetic acid. Like the pre-formed peracetic acid solution, the boron-oxygen compound which is used should be introduced into the reaction mixture in a form having a low water content. Thus, borox-hydrates having a low water content are preferred, particularly those borax-hydrates which, for example, correspond to the formula $Na_2B_4O_7 \cdot (H_2O)_{0-3}$ and have a boron content of about 17 to 21 percent by weight. This corresponds to a formal water of hydration content of 0 to 3 moles, whereby at water contents of less than 2 moles, the water is bound as structural water in $Na_2B_4O_5(OH)_4$. Borax-hydrates having a formal water of hydration content of about 1 to 2 moles are particularly preferred.

In order to produce the acetylperoxyborates according to the invention in a vacuum mixer in accordance with the foregoing process variant, it is important that seed crystals of acetylperoxyborate are added in step b2) to the reaction mixture of peracetic acid and boron-oxygen compound. By this means the reaction time and the crystallization time are advantageously reduced. The addition of the seed crystals of acetylperoxyborate in accordance with step b2) may take place during the reaction of the boron-oxygen compound with the peracetic acid solution in accordance with step b1) or it may first occur following this reaction. Any acetylperoxyborate can be utilized as seed crystals for step b2), for example coarse and/or fine portions (oversize and/or undersize particles) of acetylperoxyborate which are separated in subsequent process steps from the desired particle size fraction of acetylperoxyborates by sieving. Through the unlimited recycling of particle size fractions of acetylperoxyborate with oversize and/or undersize particles, an advantageous and complete utilization of the initially supplied raw materials can be assured.

The quantity of seed crystals which is added depends on the amount of oversize or undersize material obtained from the sieving step and as noted above is not critical. Clear effects on the reaction time and crystallization time result from adding an amount of at least about 2 weight percent, based on the total weight of the reaction mixture in step b1). If less than 2 weight percent is added, longer reaction and crystallization times must be reckoned with.

Following the foregoing conversion and addition of seed crystals, a paste of the acetylperoxyborate is formed in step b3) from the reaction mixture by progressive crystallization while mixing at temperatures of up to about 45° C., preferably at temperatures of about 35° to 40° C.

The largest portion of the solvent and other volatile components are removed from this paste in step b4) by gentle vacuum drying, optionally with addition of a lubricant. The vacuum drying is carried out, for example, at a pressure of about 10 to 100 mbar. During the vacuum drying, the product temperature is adjusted to up to about 60° C., preferably from 35° to 55° C. The solvent (acetic acid) can thereby be removed from the acetylperoxyborate paste under very gentle conditions and can be recycled to the production process for the pre-formed peracetic acid solution. In the course of the vacuum drying, the solvent content decreases, and the paste of acetylperoxyborate enters a plastic condition, the viscosity of which continues to increase during the vacuum drying. Some time during vacuum drying a phase is reached which is critical for the formation of a granular product, the break down or changeover phase, in which viscosity of the product again increases significantly. The beginning of this break down or changeover phase can be recognized by a clear increase in the electrical power requirement of the mixer. In the course of this break down or changeover phase, the acetylperoxyborate is transformed from a viscous, plastic mass to a solid product which is still kneadable by the mixer. At the end of this break down or changeover phase, the mixer breaks through this solid, yet still kneadable, condition of the acetylperoxyborate with decomposition of the kneadable paste and formation of a now crumbly acetylperoxyborate product, with which the break down or changeover phase is exceeded. Immediately after exceeding the break down or changeover phase, i.e. after the breakthrough, the size-reducing auxiliary mixing tool, preferably a studded disc mill, must be turned on for a brief period of a few minutes. This time period depends on the degree of size reduction desired and in particular, may range up to about 10 minutes. The effect of the size-reducing auxiliary mixing device is important for the formation of granular product with regard to the form of the granules and to the regulation of the grain size.

By means of the optional addition of lubricant, the energy requirements during the break down or changeover phase are decreased, and it is easier to get through the break down or changeover phase including the size reduction step. In the present invention any lubricant can be utilized which is oxidation-stable and is compatible with the reactants and products. Metal salts of fatty acids, particularly alkali and/or alkaline earth metal salts of long-chain saturated fatty acids, which preferably are unbranched and may contain up to 18 carbon atoms, especially 16 to 18 carbon atoms, are suitable. Salts of stearic acid have proved especially suitable. Fatty acid salts of the alkali and alkaline earth metals of the second and third periods of the period table of elements are especially preferred, particularly those of sodium, potassium or magnesium. Magnesium stearate is particularly preferably utilized as a metal salt of a fatty acid in the process of the present invention. The lubricant is thereby added to the acetylperoxyborate paste obtained in step b3) at the beginning of the pre-drying in step b4) in a quantity of up to 5 weight percent, preferably in a quantity of from 0.2 to 1 weight percent, based on the weight of the reaction mixture in step b1).

Following the vacuum drying in accordance with step b4), a solid, granular acetylperoxyborate particulate material is obtained which still may contain up to about 10 weight percent volatile components, for example acetic acid and/or water. To completely remove these residual volatile components, the granulate must be dried in a further drying step under more stringent drying conditions, since a further drying under vacuum conditions is very time consuming and does not lead to the required degree of dryness. The subsequent drying clearly influences the stability of the product in a positive manner. The aforedescribed first drying step, namely the pre-drying under vacuum conditions in accordance with step b4), is thus followed in step b5) by a second drying step, particularly for example an air drying step. The drying of the acetylperoxyborate product from step b4) is therefore carried out under normal pressure and at product temperatures up to 80° C., preferably up to about 60° C., until the residual volatile components (e.g. acetic acid, water) are completely removed from the product.

The subsequent drying in process step b5) can be carried out according to two variants. In a first variant b5.1) the acetylperborate product from the vacuum drying in step b4) is initially completely dried, e.g. by air drying, and thereafter the desired particle size fraction of the acetylperborate is separated by sieving. In a second variant b5.2) the desired particle size fraction of the acetylperoxyborate granulate is initially separated by sieving the pre-dried acetylperoxyborate product from step b4), and only this fraction with the desired particle size is subjected to subsequent drying, e.g. by air drying.

The separated fraction of the acetylperoxyborate granulate with oversize and/or undersize granules (coarse fractions and fine fractions) can subsequently be recycled to the production process in an advantageous manner as seed crystals for step b2). The air drying can be carried out, for example, by means of the usual, conventional process, preferably by drying in a fluidized bed. In process variant b5.1) the subsequent drying can optionally also be carried out in the vacuum mixer, insofar as the mixer is additionally equipped with a system for introducing dry air and carrying away exhaust air.

The process of the invention for producing acetylperoxyborates in accordance with process steps b1) through b5) has particular advantages. In particular, this process makes it possible to significantly shorten the reaction time for forming the acetylperoxyborates in comparison to the other process variants. The two stage drying makes it possible to completely remove volatile components, such as acetic acid and water, from the reaction product under gentle conditions. The major portion of the volatile components are thereby initially removed under mild conditions in a vacuum drying step, while only a small portion of up to about 10 weight percent of volatile components is finally completely removed under the more stringent conditions of the second drying step. In this way, very stable products with long storage lives are obtained. Further, the product is initially produced in a granular form, so that further granulation processes are superfluous. The product can thus be conveyed directly to a further use, optionally after coating with an overcoat.

The processes and process variants described above enable the acetyl peroxyborate compounds of the invention to be produced in an advantageous manner. In these production processes, the compounds of the invention are generally obtained in the form of colorless powders, or optionally as colorless granular products, and can then be processed further for their intended use by known measures. For example, they can be processed by known granulation or agglomeration processes to produce appropriate application forms such as, for example, cut extruded sections, pellets, granules, briquettes, tablets or granular products having a desired grain size distribution, etc. If desired, acetyl peroxyborate compound products obtained by granulation or agglomeration can additionally be coated by known coating processes. In order to prepare granular products, agglomerates or tablets, commonly used auxiliary agents such as binders, slips, disintegration promoting agents, stabilizers, etc., can be used. Moreover, in order to protect the acetyl peroxyborate compound product of the invention from moisture in certain applications, it can additionally be fused into a film, e.g. standard household polyethylene film. This is particularly advantageous for bleaching applications (e.g. dry bleach, stain removal salt) or disinfectant applications, since this facilitates application of an appropriate dosage.

The acetyl peroxyborate compounds of the invention have a number of advantages. As compounds which release peracetic acid, for example, they exhibit an excellent bleach performance even vis-a-vis difficult stains such as red wine or tea. Their bleaching performance not only equals that of DPDDA systems, but significantly exceeds that of conventional perborate/TAED systems. This high bleaching performance is also achieved in liquid detergents and in comparison with conventional stain removal salts (percarbonate/TAED systems). Moreover, the bleaching agent, namely peracetic acid, is made available more rapidly by the compounds according to the invention than by the standard perborate/TAED bleach systems. Also, the acetyl peroxyborate compounds according to the invention have advantages during application as disinfectants. The compounds according to the invention correspond to peracetic acid in terms of their microbicidal effect but are more advantageous than peracetic acid because of their solid form. The compounds according to the invention can thus be apportioned easily for disinfectant use, e.g. in the form of tablets or pre-packaged portions of granular material.

Granules of the acetyl peroxyborate compounds according to the invention also have advantages during use as stain removal salts or bleaching agents in portion form (e.g. heat-sealed in film or in deep-drawn cups closed with laminated film) particularly when used in combination with liquid detergents. When used together with liquid detergents, these bleaching agents can then be added in portions to the wash process separately from the liquid detergent which contains no bleaching agent.

The following examples are intended to further illustrate the invention without restricting its scope. The abbreviations used have the following meanings:

PAA=peracetic acid;
IR=infra-red spectroscopy;
NMR=nuclear magnetic resonance spectroscopy;
CP/MAS=cross polarization/magic angle spinning;
DSC=differential scanning calorimetry;
Borax B=$Na_2B_4O_7 \cdot (H_2O)_{2-3}$ obtained from borax A (=$Na_2B_4O_7 \cdot 10H_2O$) by two hours drying in a circulating air oven at 150° C.
Borax C=$Na_2B_4O_7 \cdot (H_2O)_{0-1}$ obtained from borax B by an additional one hour drying at 400° C.
PBS-1=sodium perborate monhydrate;
Oa=active oxygen=avox;
DPDDA=diperoxydidecanedioic acid;
TAED=tetraacetylethylenediamine;
PBS-4=sodium perborate tetrahydrate;
PCS=sodium percarbonate.

EXAMPLE 1

10 g of sodium perborate monohydrate (15% by weight active oxygen) were reacted with 30 g of acetic acid (96% by weight) for 20 hours at 35° C. with stirring in a stirred vessel to the consistency of a homogeneous paste and subsequently dried for two hours at 40° C. under vacuum in a water-jet pump (molar ratio of the reactants: 1:5). 15 g of an acetyl peroxyborate were obtained as a dry product in the form of a white powder having the following composition and properties:

Active oxygen content: 3.5% by wt.
Content of PAA liberatable in water: 16% by wt.
Content of $H_2O_2$ liberatable in water: 0.2% by wt.

EXAMPLE 2

40 g of a sodium peroxyborate having a molar ratio of sodium to boron to active oxygen of 0.6:1:1.1 were reacted with 120 g acetic acid (96% by weight) for 20 hours at 30° C. with stirring to form a paste. After the reaction the molar ratio of Na:B:Oa:acetic acid in the reaction mixture was 0.6:1:1.1:4. The reaction product was subsequently dried under vacuum at 40° C. The resulting dried product consisted of 69 g of an acetyl peroxyborate having the following composition and properties:

Active oxygen content: 6.4% by wt.
Content of PAA liberatable in water: 25% by wt.
Content of $H_2O_2$ liberatable in water: 2.4% by wt.
DSC: endothermic peak (maximum) at approx. 160° C.; exothermic peak (maximum) at approx. 178° C.

EXAMPLE 3

30 g of borax C (20.6% by weight boron) were reacted with 137 g of acetic acid (99.8% by weight) and 23 g of hydrogen peroxide (85% by weight) in a molar ratio of Na:B:Oa:acetic acid of 0.5:1:0.97:3.92 for 15 hours at 30° C. while stirring to form a paste which was subsequently dried at 40° C. under a water-jet vacuum. 73 g of an acetyl peroxyborate were obtained as a dried product having the following composition and properties:

Active oxygen content: 6.1% by wt.
Content of PAA liberatable in water: 26.1% by wt.
Content of $H_2O_2$ liberatable in water: 1.2% by wt.
IR (KBr, $cm^{-1}$): 1748; 1660
$^{13}$C-CP/MAS-NMR: 18.6 ppm
DSC: endothermic peak (maximum) at approx. 150° C.; exothermic peak (maximum) at approx. 180° C.; (additional endothermic peak at approx. 215° C.).

EXAMPLE 4 a) Pre-formed peracetic acid was prepared. For this purpose, 170 g of acetic acid (99.8%-by weight) and 30 g of 85% by weight hydrogen peroxide were stirred with an addition of 1 g concentrated sulfuric acid for 1.5 hours at 35° C. 200 g of a pre-formed peracetic acid solution having a peracetic acid content of 24.5% by weight and a residual free hydrogen peroxide content of 1.4 wt-% were obtained.

b) 150 g of the peracetic acid solution obtained under a) were reacted with 24 g of borax C (20.9% by weight boron) corresponding to a Na:B:PAA molar ratio of 0.5:1:1 to form a homogeneous suspension and subsequently dried at 40° C. under a water-jet vacuum. 55 g of an acetyl peroxyborate in the form of a powder having the following composition and properties were obtained as the dried product:

Active oxygen content: 6.6% by wt.
Content of PAA liberatable in water: 28% by wt.
Content of $H_2O_2$ liberatable in water: 1.6% by wt.

EXAMPLE 5

40 g of a peracetic acid solution prepared according to Example 4a) were reacted with 20 g of borax C (20.9% by weight boron) corresponding to a Na:B:PAA molar ratio of 0.5:1:0.5 for 3 hours at 35° C. to form a paste. The resulting paste was washed twice on a suction filter with 50 ml of ethanol and subsequently dried for 2.5 hours at 50° C. in a circulating air drying chamber. An acetyl peroxyborate was obtained as the dried product in the form of an extremely stable white powder having the following composition and properties:

Active oxygen content: 6.1% by wt.
Content of PAA liberatable in water: 28% by wt.
Content of $H_2O_2$ liberatable in water: 0.4% by wt.

IR (KCl, cm$^{-1}$): 1748; 1661

$^{13}$C-CP/MAS-NMR: 18.5 ppm

DSC: endothermic peak (maximum) at approx. 160° C.; exothermic peak (maximum) at approx. 172° C.

EXAMPLE 6

Initially, 40 g of a sodium peroxyborate having a molar ratio of sodium to boron of 0.6:1 and a molar ratio of boron to active oxygen of 1:1.1 (active oxygen content 20% by weight) and 120 g acetic acid (96% by weight) were reacted for 20 hours with stirring at 30° C. to form a homogeneous paste. The molar ratio of Na:B:Oa:acetic acid in the reaction mixture was thus 0.6:1:1.1:4.2. By adding 100 ml acetic acid ethyl ester, the resulting paste was subsequently converted into a sprayable suspension which was then sprayed in a spray drier at off-gas temperatures of 100° to 105° C. The resulting spray-dried product was a dry acetylperoxyborate having the following composition and properties:

Active oxygen content: 6.6% by wt.

Content of PAA liberatable in water: 25% by wt.

Content of $H_2O_2$ liberatable in water: 2.8% by weight

DSC: endothermic peak (maximum) at approx. 152° C.; exothermic peak (maximum) at approx. 170° C.

EXAMPLE 7

61.4 g of a peracetic acid solution prepared according to example 4a) were reacted with 20 g borax B (containing 16.3% by weight boron and approx. 3 molecules of water of hydration corresponding to borax trihydrate) corresponding to a Na:B:PAA molar ratio of 0.5:1:0.67 were reacted for 3 hours at 35° C. to form a paste. Subsequently, the paste was converted with 150 ml acetic acid ethyl ester to a sprayable suspension which was then sprayed in a spray drier at off-gas temperatures of 100° to 110° C. The resulting spray-dried product was an acetyl peroxyborate having the following composition and properties:

Active oxygen content: 4.6% by wt.

Content of PAA liberatable in water: 21.5% by wt.

Content of $H_2O_2$ liberatable in water: 0.1% by wt.

DSC: endothermic peak (maximum) at approx. 150° C.; exothermic peak (maximum) at approx. 175° C.

EXAMPLE 8

10 g of borax C (20.8% by weight boron) were added to 30.3 g of a peracetic acid solution prepared according to example 4a) and stirred for 3 hours at 35° C. 100 ml of ethyl acetate were subsequently added to the resulting suspension, and the suspension was spray-dried in a conventional spray drier at an off-gas temperature of 115° C. A dry acetyl peroxyborate having the following composition and properties was obtained as a spray-dried product:

Active oxygen content: 5.7% by wt.

Content of PAA liberatable in water: 25% by wt.

Content of $H_2O_2$ liberatable in water: 1% by weight

DSC: endothermic peak (maximum) at approx. 140° C.; exothermic peak (maximum) at approx. 170° C.

EXAMPLE 9 a) A mixture was initially prepared from 84 parts by weight technical grade acetic acid (96% by weight), 15 parts by weight hydrogen peroxide (85% by weight) and 1 part by weight concentrated sulfuric acid. The mixture was stirred for approximately 1.5 hours at 35° C. Subsequently, acetic anhydride (17 parts by weight based on the total quantity) was added to this mixture and stirring was continued for a further hour at 35° C. The resulting pre-formed peracetic acid solution contained 22% by weight peracetic acid, 71% by weight acetic acid, 0.5% by weight hydrogen peroxide and 6.5% by weight water.

b) The peracetic acid solution prepared above was reacted with borax B (18% by weight boron) having a boron to peracetic acid molar ratio of 1:0.55 for 3 hours at 40° C. A product with a consistency ranging from a paste to a solid was obtained which, by drying in a rotary evaporator, gave an acetyl peroxyborate having a content of peracetic acid liberatable in water of 28% by weight. The other analytical data corresponded to the product described in Example 4.

EXAMPLE 10

3290 g of a pre-formed peracetic acid solution according to Example 9a) were reacted with 1000 g of borax B (18.3% by weight boron) and 35 g 1,1-hydroxyethane diphosphonic acid (60% by weight in $H_2O$) in an intensive vacuum mixer under normal pressure for 4 hours at 35° C. to form a paste. Subsequently, the paste was dried under vacuum in this mixer for 1 hour at 50° C. During this process, the product was granulated to form a granular material with particle sizes of approximately 1 to 3 mm. The resulting granular product was subsequently additionally dried for 3 hours at 50° C. in a circulating air drying oven. A dry free-flowing granular product was obtained having the following composition and properties:

Active oxygen content: 5.6% by wt.

Content of PAA liberatable in water: 26% by wt.

Content of $H_2O_2$ liberatable in water: 0.2% by wt.

DSC: endothermic peak (maximum) at approx. 167° C; exothermic peak (maximum) at approx. 181° C.

EXAMPLE 11

282 g of a pre-formed peracetic acid solution containing 25% by weight PAA and 1.8% by weight $H_2O_2$ were added to a mixture of 64.4 g of boron oxide ($B_2O_3$) and 76.7 g of sodium acetate. The Na:B:PAA molar ratio of the reaction mixture was 0.5:1:0.5. The reaction temperature was maintained at 35° C. After 1 hour, a paste was obtained which was initially dried for 2 hours at 40° C. under a water-jet vacuum and subsequently dried for a further 1 hour at 50° C. The resulting acetyl peroxyborate had a content of PAA liberatable in water of 27% by weight.

EXAMPLE 12

The dry stability of the products obtained in Examples 1 to 11 was investigated. To determine their dry stability, the samples to be examined were exposed to the conditions indicated in Table 1, and the subsequent active oxygen loss due to decomposition of peracetic acid was determined.

The determination of the active oxygen content before and after the treatment indicated in Table 1 was carried out by known titrimetric methods. Table 1 provides an overview of the conditions used and the results obtained.

TABLE 1

Stability tests, Example 12

| Example No. | Test conditions | Loss of active oxygen in % |
|---|---|---|
| | a) Open storage in a drying cabinet | |
| 1 | 60° C./4 Weeks | 6 |
| 2 | 60° C./4 Weeks | 5 |
| 3 | 60° C./4 Weeks | 15 |
| 9 | 60° C./5 Weeks | 6 |
| 9 | 60° C./6 Months | 16 |
| | b) Short term stability at elevated temperature | |
| 5 | 100° C./1 h | 4.4 |
| 6 | 100° C./1 h | 11 |
| 7 | 100° C./1 h | 8 |
| 8 | 100° C./1 h | 10 |
| 10 | 100° C./1 h | 5 |
| PBS-1° (comparison) | 100° C./1 h | 7–10 |
| | c) Storage in a closed polyethylene flask | |
| 2 | 20° C./420 days | 13 |
| 5 | 20° C./205 days | 9 |
| 8 | 20° C./337 days | 14 |
| 10 | 20° C./120 days | 1.8 |

(°Active oxygen from $H_2O_2$)

EXAMPLE 13

The effectiveness of the acetyl peroxyborate compounds according to the invention as bleaching agents in heavy duty detergents (a) and as bleaching wash additives (b) was determined in comparison with conventional bleaching agent systems using exemplary test stains.

The wash tests were carried out either in a laboratory apparatus of the Linitest-type or in a commercially available front loading domestic washing machine of the Miele Sensor-Electronik W 784 type. The wash temperatures were 40° C. or 60° C. Each of the fabrics with test stains was washed together with 2 kg of white woven hand towels as an additional load.

The following commercially available woven fabric sections with tea or red wine contamination covering the entire surface were used as test fabrics:

test fabric WFK Tea 106; pure cotton test fabric from Waeschereiforschung Krefeld with tea staining;

test fabric EMPA Red wine 114; pure cotton test fabric from the Swiss Federal Material Testing Institute at St. Gallen (Switzerland) with red wine staining.

In addition, a test fabric prepared in-house was used:

cotton/polyester test fabric: fabric blend consisting of (50/50) cotton and polyester weighing 240 $g/m^2$ and tea test staining (cot/pe tea) or red wine staining (cot/pe red wine).

A commercially available phosphate-free, zeolite-containing base powder without any source of active oxygen, a commercially available heavy duty branded detergent containing active oxygen, and a commercially available liquid detergent were used as the washing agents. The quantities used depended on the manufacturers' dosage recommendations. The bleaching agent according to the invention or the conventional bleaching system used for comparison purposes was added to the wash components. The compounds according to the invention and the comparison materials were added in equal amounts by weight (equivalent weight) or in amounts yielding equal amounts of active oxygen (Oa equivalent). The following bleaching agent systems were used as comparative examples:

Sodium perborate tetrahydrate/TAED for in situ preparation of peracetic acid according to a standard formulation having an average content of 20% by weight sodium perborate tetrahydrate and 4% by weight TAED in fully formulated heavy duty detergents;

DPDDA (diperoxydodecanedioic acid) as an example of a conventional solid percarboxylic acid;

a stain removal salt composed of sodium percarbonate or sodium perborate monohydrate and TAED.

The wash result was determined in terms of the degree of bleaching in percent as an average value obtained from 10 individual measurements. The determination was based on non-stained reference fabric being considered as 100% and stained unwashed fabric as being 0%. The degree of bleaching was determined by brightness measurements with a reflectance meter at a light wavelength of 456 nm against a barium standard. The following results were obtained:

a) Effectiveness of the compounds according to the invention in heavy duty detergents.

For the wash tests and results summarized in the following Table 2, the compounds according to the invention and the comparison materials were incorporated into a commercially available, phosphate-free base detergent powder which did not contain any source of active oxygen.

TABLE 2

| | Bleaching agent | | | Degree of bleaching in % for fabrics of | | | |
|---|---|---|---|---|---|---|---|
| | | | | Cotton | | Cotton/Polyester | |
| No. | Type | Relative Quantity | Conditions | Tea[1] | Red wine[2] | Tea[3] | Red wine[4] |
| A1 | PBS-4/TAED | Oa equiv. | 40° C., washing machine | 34 | — | | 23 |
| A2 | DPDDA | " | 40° C., washing machine | 38 | — | | 28 |
| A3 | Acetylper-oxyborate | " | 40° C., washing machine | 42 | — | — | 28 |
| B1 | DPDDA | Weight equivalent | 60° C., washing machine | 25 | 22 | 13 | 8 |
| B2 | Acetylper-oxyborate | " | 60° C., washing machine | 47 | 34 | 36 | 22 |
| C1 | — | — | 60° C., Linitest | 22 | 12 | — | — |
| C2 | PCS | Weight equivalent | " | 27 | 18 | — | — |
| C3 | PBS-4/TAED | " | " | 27 | 18 | — | — |
| C4 | Acetylper-oxyborate | " | " | 52 | 32 | — | — |
| C5 | Acetylper-oxyborate | Oa equiv. to C2 | " | 39 | 24 | — | — |

A1, A2, B1, C1 to C3 = State of the art; A3, B2, C4 and C5 according to the invention
[1] Test fabric WFK Tea 106
[2] Test fabric EMPA Red wine 114
[3] Test fabric (50/50) cotton/polyester with tea stain prepared in-house
[4] Test fabric (50/50) cotton/polyester with red wine stain prepared in-house b) Effectiveness of the compounds according to the invention as bleaching additives For the wash tests and results summarized in the following Table 3, the compounds according to the invention and the comparison materials were incorporated into the following wash compositions:

W=fully formulated, commercial brand detergent (with bleaching component)

L=commercially available liquid detergent.

TABLE 3

Effectiveness of the bleaching additive, Example 13b)

| | Bleaching agent | | | | Degree of bleaching % in for fabrics of | | | |
|---|---|---|---|---|---|---|---|---|
| | | | | | Cotton | | Cotton/BW | |
| No. | Type | Relative quantity | I | Conditions | Tea[1] | Red wine[2] | Tea[3] | Red wine[4] |
| D1 | — | — | W | 40° C., washing machine | 33 | 20 | 22 | 16 |
| D2 | Stain removal salt/PCS | Oa-equivalent | " | " | 33 | 23 | 24 | 16 |
| D3 | Acetylper-oxyborate | " | " | 40° C., washing machine | 42 | 28 | 31 | 23 |
| E1 | — | — | W | 60° C., washing machine | 44 | 35 | 27 | 16 |
| E2 | Stain removal salts/PCS | Weight equivalent | " | " | 50 | 41 | 37 | 24 |
| E3 | DPDDA | " | " | 60° C., washing machine | 49 | 40 | 32 | 21 |
| E4 | Acetylper-oxyborate | " | " | 60° C., washing machine | 60 | 44 | 48 | 27 |
| E5 | Acetylper-oxyborate | 40% of the amount of Oa at E2 | " | " | 57 | 39 | 39 | 23 |
| F1 | — | — | L | 40° C. Unitest | 30 | 19 | 32 | 15 |
| F2 | Stain removal salt/PCS | — | " | " | 20 | 11 | 18 | 17 |
| F3 | Acetylper-oxyborate | 33% of the amount of Oa at F2 | " | " | 49 | 30 | 48 | 28 |
| G1 | — | — | L | 60° C. Linitest | 22 | 18 | — | — |
| G2 | Stain removal salts/PCS | Weight equivalent | " | " | 8 | 9 | — | — |
| G3 | Stain removal salt/PCS | " | " | " | 16 | 13 | — | — |
| G4 | Acetylper-oxyborate | Oa equivalent to G2 | " | " | 34 | 26 | — | — |
| G5 | Acetylper-oxyborate | Oa equivalent to G3 | " | " | 26 | 19 | — | — |

D1, D2, E1 to E3, F1, F2, G1 to G3 = State of the art
D3, E4 and E5, F3, G4 and G5 = according to the invention
[1] Test fabric WFK Tea 106
[2] Test fabric EMPA Red wine 114
[3] Test fabric (50/50) cotton/polyester with tea stain prepared in-house
[4] Test fabric (50/50) cotton/polyester with red wine stain prepared in-house

EXAMPLE 14

The disinfectant effect of acetyl peroxyborate compounds according to the invention was investigated, particularly with regard to their microbicidal effectiveness (DLG suspension test). The period of activity was 2.5 min., the rate of destruction was determined as a function of the incubation temperature (20° C. and 40° C.) and the pH. The test organisms used were *Klebsiella aerogenes, Pseudomonas fluorescens, Staphylococcus aureus*, and *Streptococcus faecalis*. At 20° C. and a pH of 2.0, the acetyl peroxyborates of the invention used in a concentration of 0.008% (80 mg/liter) safely destroyed the four bacteria tested in 2.5 minutes. It thus provides better performance than the commonly available disinfectants which contain approximately 8.4% PAA and 17% by weight $H_2O_2$. At a pH of 5.6, the bacteria tested are safely destroyed with a concentration of 0.01% by weight. By increasing the temperature from 20° C. to 40° C., the microbicidal effect can be increased slightly. In a further series of tests, *Pseudomonas aeruginosa* was used as test organism and was safely destroyed at room temperature with a concentration of 74 mg/l. Further, it was found that the acetyl peroxyborates of the invention are effective against fungi and viruses as well as bacteria.

The results of the disinfection tests establish that the acetyl peroxyborates of the invention are excellent disinfectants, especially in the acid to neutral pH range. They are consequently useful as disinfectants in medical clinics, in veterinary medicine, in animal stalls or in dairy sanitation.

EXAMPLE 15

| Starting materials: | |
|---|---|
| peracetic acid solution containing 21.4% PAA and 1% $H_2O_2$ produced from: | |
| acetic acid 99% | 19 kg |
| hydrogen peroxide 85% | 3.4 kg |
| acetanhydride | 3.2 kg |
| sulfuric acid | 0.22 kg |
| turpinal SL | 0.3 kg |
| borax (B = 18.37%) | 8.02 kg |
| acetylperoxyborate seed crystals | 2.0 kg |
| magnesium stearate | 0.15 kg |

(all percent values expressed in weight percent).

a) Pre-formed peracetic acid:

Hydrogen peroxide reacted with sulfuric acid and acetanhydride were simultaneously, but separately, added to acetic acid in such a way that a temperature of about 25° C. was maintained. After addition of 1-hydroxyethane-1,1-diphosphonic acid (turpinal SL) the reaction mixture was heated for one hour at 35° C. A solution of peracetic acid with a low water content having the following representative composition was obtained:

21.4 weight percent PAA 1.0 weight percent $H_2O_2$.

b) Boron raw material (=boron-oxygen compound):

In order to produce the boron raw material, borax pentahydrate was dried in a dryer to an analytically determined boron content of ca. 18.4 weight percent.

c) Acetylperoxyborate:

The raw materials produced in steps a) and b) of this example were combined in a vacuum turbulent mixer, together with the undersize and oversize acetylperoxyborate particles obtained from a final sieving step, and reacted at 35° C. to form a paste. The mixer was equipped with rotating mixing wings (Fr>1), and a rotating studded disk mill (Fr>>1), as well as a heating and cooling jacket. The reaction time was about 50 minutes. Before the beginning of the vacuum drying, magnesium stearate was added, and excess acetic acid and water were removed at a product temperature of 35° to 55° C. (at about 60° to 70° C. heating of the jacket) and at a vacuum of 50 to 100 mbar. The circumferential speed of the mixing wings during the reaction and drying was approximately 4 meters per second (FR=approx. 9). During this drying the viscosity increased until it reached the break down or changeover phase, at which time the circumferential speed of the mixing wings was reduced to approximately 1.5 meters per second (Fr approximately 1.1). After exceeding the break down or changeover phase, i.e. at the onset of disintegration of the mass, the studded disc mill was turned on for 10 minutes (circumferential speed approximately 22 meters per second (Fr=approx. 700). A granular particulate material thereby formed. Subsequently, the material was dried further at a circumferential speed of the mixing wings of four meters per second until the product was free flowing.

19 kg of the granular product from the aforementioned first drying step was sieved to separate particle sizes in the range from 0.4 to 5 millimeters, and the fine and coarse fractions (3.1 kg) were recycled as seed crystals to the acetylperoxyborate production step.

The sieved product granulate was subjected to subsequent drying in a second drying step. For this purpose the granulate was dried by air drying for one hour in a fluidized bed at a fluidized bed temperature of about 60° C. The drying loss amounted to about 8 to 10 weight percent. Approximately 14.3 kilograms of an acetylperoxyborate granulate were obtained having the following composition and characteristics:

sodium: 9.1 weight percent (acidimetric)

boron: 9.6 weight percent (acidimetric)

acetic acid: 23.6 weight percent (acidimetric)

peracetic acid: 26.5 weight percent (iodometric)

$H_2O_2$: 0.2 weight percent (cerometric)

Rate of dissolution:

97% after three minutes (2 g/l, 20° C., 200 rpm)

Particle size analysis:

| | |
|---|---|
| >2.5 mm | 3.4 weight percent |
| >1.0 mm | 39.4 weight percent |
| >0.8 mm | 18.4 weight percent |
| >0.63 mm | 19.9 weight percent |
| >0.4 mm | 18.2 weight percent |
| <0.4 mm | 0.7 weight percent |

Bulk density:

0.8 kg/liter

Stability determination (typical values, % = wt. %):

| | |
|---|---|
| Avox-loss at 110° C./15 hours: | 9% |
| Avox-loss in a closed container at 20° C./6 months: | 1% |
| Avox-loss in a closed container at 40° C./4 weeks: | 2–3%. |

Microcalorimetric data at 40° C. in closed glass ampules:

ca. 10 μW/g for the fully dried product ca. 400 μW/g for the predried product.

The foregoing description is merely to illustrate the invention and is not limiting. Since modifications incorporating the substance of the invention may occur to persons skilled in the art, the invention should be construed to include everything within the scope of the appended claims and equivalents.

We claim:

1. A solid acetyl peroxyborate composition having an active oxygen content of from 2 to 8% by wt. and consisting essentially of molecules of solid peracetic derivative compounds comprising acetyl groups, peracetyl groups and borate structures

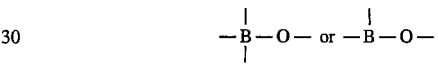

combined with each other in such a manner that the product spontaneously disintegrates in water and releases at least 10% by wt. of peracetic acid relative to the total product; said product having an infrared spectrum characterized by IR absorption bands at approximately 1650 to 1670 cm$^{-1}$ and at approximately 1740 to 1755 cm$^{-1}$, having a $^{13}$C-NMR spectrum, measured by solid body spectroscopy against an external tetramethylsilane standard, characterized by a band at 18 to 19 ppm, and upon disintegration in water, releasing no more than 4 wt. % of hydrogen peroxide relative to the total weight of the composition.

2. A compound according to claim 1, having a peracetic acid content in the range from 10 to 30% by wt.

3. A compound according to claim 1, having a hydrogen peroxide content, which can be liberated upon dissolution of the acetyl peroxyborate compound in water, of less than 3% by wt.

4. A compound according to claim 3, having a hydrogen peroxide content, which can be liberated upon dissolution of the acetyl peroxyborate compound in water, of less than 1.5% by wt.

5. A compound according to claim 1, having a peracetic acid content, which can be liberated upon dissolution of the acetyl peroxyborate compound in water, of from 20 to 30% by wt.

6. A compound according to claim 1, exhibiting a $^{13}$C-NMR spectrum characterized by a band at approximately 18.5 ppm.

7. A compound according to claim 1, exhibiting a differential calorimetry diagram which begins exothermically at approximately 135° to 140° C. and continues exothermically with an exothermic peak at approximately 170° to 185° C.

8. A solid product according to claim 1, further comprising a lubricant.

9. A solid washing, bleaching or disinfecting composition comprising:
   an effective oxidizing amount of a solid acetyl peroxyborate compound having an active oxygen content of from 2 to 8% by wt.; a peracetic acid content, which can be liberated upon dissolution of the acetyl peroxyborate compound in water, of at least 10% by wt., and a hydrogen peroxide content of less than 4% by wt., and
   at least one conventional solid washing, bleaching or disinfecting agent.

10. A composition according to claim 9, in the form of powdered or granular material in a sachet or in the form of tablets fused into a film.

11. A process for producing a solid acetyl peroxyborate compound comprising:
   a) reacting a solid boron-oxygen compound selected from the group consisting of mixtures of boric acid or boron oxide and an alkaline sodium salt, sodium polyborates containing no more than three molecules of water of hydration, sodium metaborate, borax anhydride, and sodium perborate having a Na:B molar ratio of from 0.3:1 to 1:1, with acetic acid and hydrogen peroxide; or
   b) reacting a solid boron-oxygen compound selected from the group consisting of mixtures of boric acid or boron oxide and an alkaline sodium salt, sodium polyborates containing no more than three molecules of water of hydration, sodium metaborate, borax anhydride, and sodium perborate having a Na:B molar ratio of from 0.3:1 to 1:1, with a solution of peracetic acid in acetic acid; or
   c) reacting acetic acid with a solid sodium perborate having a Na:B molar ratio of from 0.3:1 to 1:1,
   whereby a viscous solution, a suspension or a paste is obtained; and
   drying the resulting viscous solution, suspension or paste to recover the solid acetyl peroxyborate compound.

12. A process according to claim 11, wherein acetic anhydride is added to reacting step a) or b).

13. A process according to claim 11, wherein an alkaline sodium salt is added in the reacting step.

14. A process according to claim 11, wherein said reacting step is carried out at a temperature in the range from ambient temperature up to 60° C.

15. A process according to claim 14, wherein said reacting step is carried out at a temperature in the range from 30° to 45° C.

16. A process according to claim 11, wherein a solid boron-oxygen compound is reacted with acetic acid and hydrogen peroxide in a molar ratio of boron to acetyl groups to hydrogen peroxide of 1:(1 to 5):(0.2 to 2).

17. A process according to claim 11, wherein a solid boron-oxygen compound is reacted with a solution of peracetic acid in acetic acid in a molar ratio of boron to peracetic acid of 1:(0.2 to 2).

18. A process according to claim 17, wherein the molar ratio of boron to peracetic acid is 1:(0.5 to 1).

19. A process according to claim 11, wherein acetic acid is reacted with a solid boron-oxygen compound containing peroxygen in a molar ratio of peroxygen-containing boron-oxygen compound to acetyl groups of 1:(1 to 10).

20. A process according to claim 19, wherein the molar ratio of peroxygen-containing boron-oxygen compound to acetyl groups is 1:(2 to 6).

21. A process according to claim 11, wherein a solid boron-oxygen compound is reacted with acetic acid and with hydrogen peroxide having an $H_2O_2$ content of at least 70 wt-%.

22. A process according to claim 11, wherein said solid boron-oxygen compound is boron oxide or borax having a water of hydration content of 0 to 3 water molecules.

23. A process according to claim 11, wherein acetic acid is reacted with a sodium perborate having a water of hydration content of 0 to 3 water molecules and a Na:B molar ratio of 0.3:1 to 1:1.

24. A process according to claim 23, wherein said sodium perborate is sodium perborate monohydrate, sodium perborate, or a mixture thereof and has a Na:B molar ratio of 0.4:1 to 0.7:1.

25. A process according to claim 11, wherein an acetyl peroxyborate compound obtained in paste form or by intermediate drying is washed before final drying with at least one solvent selected from the group consisting of lower alcohols and acetate esters of lower alcohols.

26. A process according to claim 11, wherein in a mixer equipped with a rotating mixing tool, a size reducing mixing assisting tool characterized by a Froude number Fr>1, a heat exchanger for cooling or heating and a vacuum device, the following steps are carried out:
   b1) reacting a pre-formed solution of peracetic acid in acetic acid with a boron-oxygen compound having a low water content in such a way that the temperature does not exceed 40° C.;
   b2) adding seed crystals of acetylperoxyborate;
   b3) mixing at temperatures up to about 45° C., whereby a paste of acetylperoxyborate is formed;
   b4) pre-drying said paste under vacuum at a temperature of at most about 60° C. until a granular acetylperoxyborate is formed, and during said pre-drying after going through a changeover phase from plastic to granular solid material at the onset of disintegration of substantially pre-dried acetylperoxyborate paste, activating said size reducing mixing assisting tool for a period of up to 10 minutes, and
   b5) completely drying the pre-dried acetylperoxyborate from step b4) at standard pressure and at a temperature of up to about 80° C. and separating a desired particle size fraction by sieving;
   whereby acetylperoxyborate is obtained in the form of a solid, granular, free-flowing particulate material.

27. A process according to claim 26, wherein pre-dried acetylperoxyborate paste is first sieved to separate the desired particle size fraction from fractions of coarser and finer material, and the desired particle size fraction is subsequently completely dried.

28. A process according to claim 26, wherein pre-dried acetylperoxyborate paste is first completely dried, and the completely dried material is subsequently sieved to separate a desired particle size fraction from fractions of coarser and finer material.

29. A process according to claim 26, wherein said complete drying is carried out at a temperature up to about 60° C.

30. A process according to claim 26, wherein said size reducing assisting tool is characterized by a Froude number Fr which is very much greater than one.

31. A process according to claim 26, further comprising adding a lubricant to said paste after formation thereof and prior to pre-drying.

32. A process according to claim 31, wherein said lubricant comprises at least one long-chain fatty acid salt of a metal selected from the group consisting of the alkali metals and the alkaline earth metals.

33. A process according to claim 32, wherein said lubricant is magnesium stearate.

34. A process according to claim 31, wherein said lubricant is added in an amount of up to 5 weight percent based on the weight of the reaction mixture in step b1).

35. A process according to claim 34, wherein said lubricant is added in an amount of from 0.2 to 1 weight percent based on the weight of the reaction mixture in step b1).

36. A process according to claim 26, wherein said pre-drying is carried out at a temperature in the range from 35° to 55° C.

37. A process according to claim 26, wherein said boron-oxygen compound in step b1) is a borax hydrate with a low water content corresponding to the formula $Na_2B_4O_7 \cdot (H_2O)_{0-3}$.

38. A process according to claim 37, wherein said boron-oxygen compound is a borax-hydrate containing from 1 to 2 molecules of water of hydration.

39. A process according to claim 26, wherein in step b2) the seed crystals are added by recycling fine and coarse fractions obtained by sieving in step b5) in an amount of at least 2 weight percent based on the weight of the reaction mixture in step b1).

40. A solid acetyl peroxyborate composition having an active oxygen content of from 2 to 8% by wt. and consisting essentially of molecules of solid peracetic derivative compounds comprising acetyl groups, peracetyl groups and borate structures

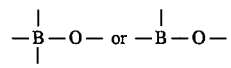

combined with each other in such a manner that the product spontaneously disintegrates in water and releases at least 10 wt-% of peracetic acid relative to the total weight of the composition, said composition being produced by a process comprising the steps of:

A) reacting in the presence of acetic acid
a solid boron oxygen compound selected from the group consisting of mixtures of boric acid or boron oxide and an alkaline sodium salt, sodium polyborates containing no more than three molecules of water of hydration, sodium metaborate, borax anhydride, and sodium perborate having a Na:B molar ratio of from 0.3:1 to 1:1, with
an acetyl reagent selected from the group consisting of acetic acid, a mixture of acetic acid and hydrogen peroxide solution having a hydrogen peroxide content of at least 50 wt-%, and a solution of peracetic acid in acetic acid, with the proviso that if said acetyl reagent is acetic acid, the solid boron oxygen compound must comprise sodium perborate,
whereby a viscous solution, a suspension or a paste is obtained; and B) evaporating residual water and any excess acetic acid from said viscous solution, suspension or paste and recovering said solid composition in the form of a particulate solid.

41. A composition according to claim 40, wherein said acetyl reagent further comprises acetic anhydride.

* * * * *